US00PP09853P

United States Patent [19]

Vandenberg

[11] Patent Number: Plant 9,853

[45] Date of Patent: Apr. 8, 1997

[54] CHRYSANTHEMUM PLANT NAMED 'GOLDEN KENT'

[75] Inventor: Cornelis P. Vandenberg, Salinas, Calif.

[73] Assignee: Yoder Brothers, Inc., Barberton, Ohio

[21] Appl. No.: 547,402

[22] Filed: Oct. 24, 1995

[51] Int. Cl.[6] ..... A01H 5/00

[52] U.S. Cl. ..... Plt./78

[58] Field of Search ..... Plt./78

[56] References Cited

U.S. PATENT DOCUMENTS

P.P. 9,302 9/1995 VandenBerg ..... Plt./77
4,616,099 10/1986 Sparkes ..... 47/58

OTHER PUBLICATIONS

Broertjes, et al., 1980, "A Mutant of a Mutant of a . . . Irradiation of Progressive Radiation–Induced Mutants in a Mutation Breeding Programme with *Chrysanthemum morifolium*", Euphytica, 29:525–530.

Gosling, ed., 1979, "The Chrysanthemum Manual—6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and Rose Mutations Induced by X–rays", Am. Soc. Hort. Sci. Proc., pp. 613–620.

Broertjes, 1966, "Mutation Breeding of Chrysanthemums", Euphytica, 15:156–162.

Dowrick, et al., 1966, "The Induction of Mutations in Chrysanthemum Using X– and Gamma Radiation", Euphytica, 15:204–210.

*Primary Examiner*—Howard J. Locker
*Attorney, Agent, or Firm*—Foley & Lardner

[57] ABSTRACT

A Chrysanthemum plant named Golden Kent particularly characterized by its flat capitulum form; decorative capitulum type; yellow ray floret color; diameter across face of capitulum of 79 to 83 mm when fully opened, when grown as a single stem spray cut mum; flowering response is 55 to 58 days after start of short days; plant height is 79 to 86 cm when grown with 17 to 18 long days prior to start of short days; peduncle length of the first lateral at flowering after removing the apical bud without growth regulator applications is 5 to 10 cm; peduncle length of the fourth lateral is 13 to 18 cm; and recommended as a spray cut mum.

1 Drawing Sheet

The present invention comprises a new and distinct cultivar of Chrysanthemum, botanically known as *Dendranthema grandiflora*, and referred to by the cultivar name Golden Kent.

Golden Kent, identified as 0061 (90-928A05), is a product of a mutation induction program. The new cultivar was discovered and selected by inventor Cornelis P. VandenBerg on Mar. 2, 1994 in a controlled environment in Salinas, Calif. as one flowering plant within a flowering block established as rooted cuttings from stock plants which had been exposed as unrooted cuttings to an X-ray source of 1750 rads in Fort Myers, Fla. on Sep. 16, 1993. The irradiated parent cultivar was the cultivar Kent, disclosed in U.S. Pat. No. P.P. 9,302, and described as a decorative spray cut mum with a white ray floret color with a cream center of the flower.

The irradiation program resulting in Golden Kent had as its primary objective the expansion of color ranges of the parent cultivar Kent. The irradiation program comprised irradiation of cuttings of the parent cultivar at irradiation levels of 1500, 1750 and 2000 rads. A total of 1,143 cuttings harvested from a total of 225 irradiated plants were planted on Dec. 27, 1993. Of these, 6 initial selections were made, which selections were then revegetated and reflowered in Honselersdijk, The Netherlands. This flowering resulted in discarding 5 of the original 6 selections on Sep. 1, 1994. Two codes were reselected under different code number prior to discarding. The remaining one selection and two reselections were maintained as PIs (Possible Introductions) and further trialed in Salinas, Calif. and in Honselersdijk, The Netherlands, ultimately resulting in the decision to introduce the one remaining selection as Golden Kent. Both remaining reselections are still being trialed.

The first act of asexual reproduction of Golden Kent was accomplished when vegetative cuttings were taken from the initial selection in May of 1994 in a controlled environment in Salinas, Calif., by technicians working under supervision of Cornelis P. VandenBerg.

Horticultural examination of controlled flowerings of successive plantings has shown that the unique combination of characteristics as herein disclosed for Golden Kent are firmly fixed and are retained through successive generations of asexual reproduction.

Golden Kent has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., under greenhouse conditions which approximate those generally used in commercial greenhouse practice.

The following traits have been repeatedly observed and are determined to be basic characteristics of Golden Kent, which, in combination, distinguish this Chrysanthemum as a new and distinct cultivar:

1. Flat capitulum form.
2. Decorative capitulum type.
3. Yellow ray floret color.
4. Diameter across face of capitulum of 79 to 83 mm when fully opened, when grown as a single stem spray cut mum.
5. Flowering response is 55 to 58 days after start of short days.
6. Plant height is 79 to 86 cm when grown with 17 to 18 long days prior to start of short days.
7. Peduncle length of the first lateral at flowering after removing the apical bud without growth regulator applications is 5 to 10 cm; peduncle length of the fourth lateral is 13 to 18 cm.
8. Recommended as a spray cut mum.

The accompanying photographic drawing is a side view of a single stem cut spray mum of Golden Kent, with the colors being as nearly true as possible with illustrations of this type.

Of the commercial cultivars known to the inventor, the most similar in comparison to Golden Kent is the parent cultivar Kent. All traits of Golden Kent are similar to those of Kent, except for the ray floret color. The ray floret color of Goden Kent is yellow, while the ray floret color of Kent is white with a cream center of the flower.

In the following description color references are made to The Royal Horticultural Society Color Chart. The color values were determined on plant material grown as a single stem spray cut mum grown in Salinas, Calif. on Jul. 3, 1995.

Classification:

*Botanical.*—*Dendranthema grandiflora* cv Golden Kent.

*Commercial.*—Flat decorative spray cut mum.

INFLORESCENCE

A. Capitulum:

*Form.*—Flat.

*Type.*—Decorative

*Diameter across face.*—79 to 83 mm when fully opened.

B. Corolla of ray florets:

*Color (general tonality from a distance of three meters).*—Yellow.

*Color (upper surface).*—12B.

*Color (under surface).*—12C.

*Shape.*—Straight, oblong, ray floret tips slightly indented, cross section concave.

C. Corolla of disc florets:

*Color (mature).*—14B.

*Color (immature).*—144B.

D. Reproductive organs:

*Androecium.*—Present on disc florets only; very few disc florets; no pollen.

*Gynoecium.*—Present on both rays and disc florets.

PLANT

A. General appearance:

*Height.*—79 to 86 cm when grown in Salinas with 17 to 18 long days prior to start of short days.

B. Foliage:

*Color (upper surface).*—147A.

*Color (under surface).*—147B.

*Shape.*—Lobed, slightly serrated.

What is claimed is:

1. A new and distinct Chrysanthemum plant named Golden Kent, as described and illustrated.

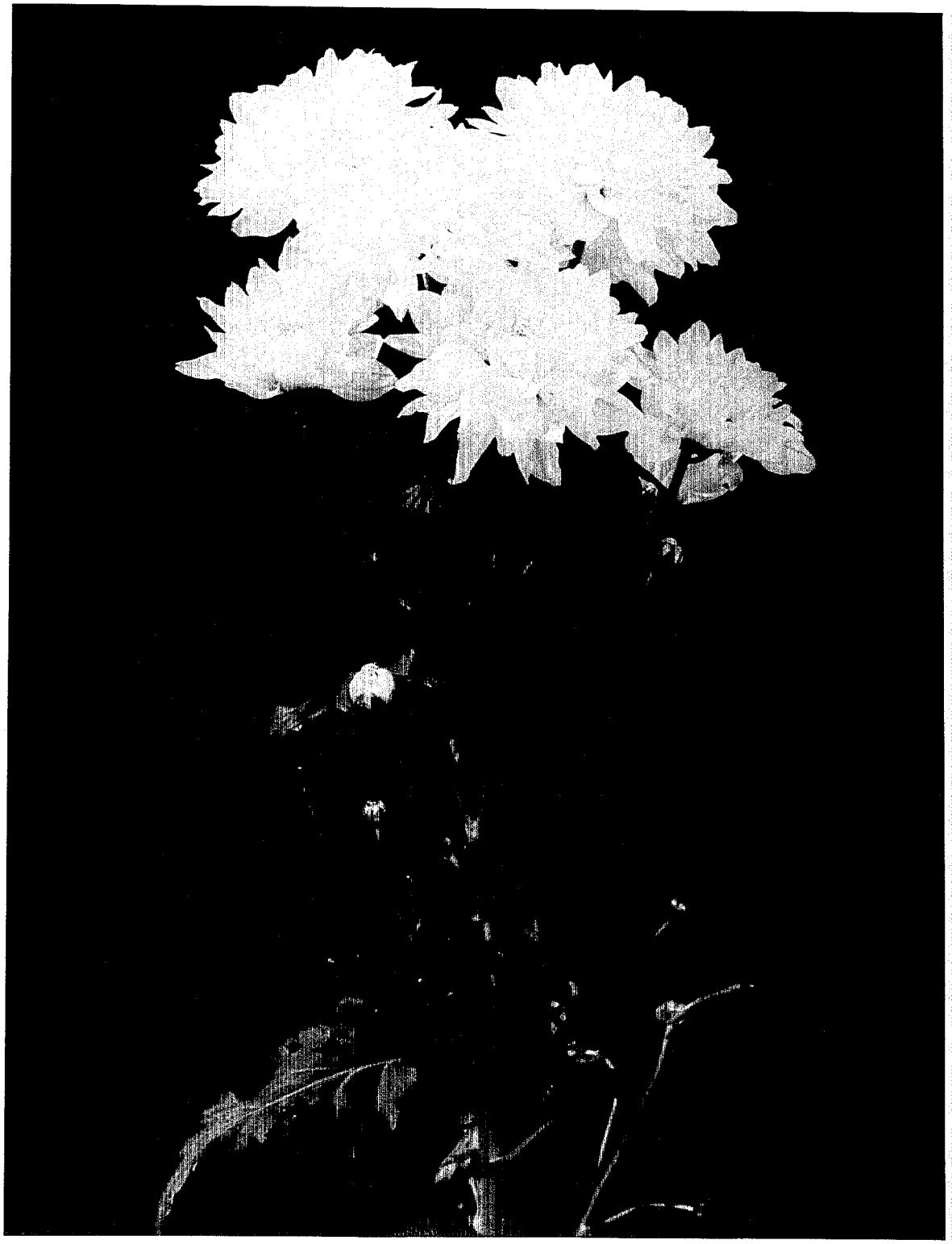

* * * * *